United States Patent
Khieu et al.

(10) Patent No.: US 8,480,636 B2
(45) Date of Patent: Jul. 9, 2013

(54) CATHETER WITH ASPIRATION PASSAGEWAY

(75) Inventors: Xuan Khieu, Maple Grove, MN (US); Richard E Stehr, Stillwater, MN (US); Thao T. Nguyen, Bloomington, MN (US); Linda Nemec, Andover, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 549 days.

(21) Appl. No.: 11/647,278

(22) Filed: Dec. 29, 2006

(65) Prior Publication Data

US 2007/0270767 A1 Nov. 22, 2007

Related U.S. Application Data

(60) Provisional application No. 60/800,861, filed on May 17, 2006.

(51) Int. Cl.
*A61M 5/00* (2006.01)

(52) U.S. Cl.
USPC ............ 604/264; 604/527; 604/528; 604/529

(58) Field of Classification Search
USPC ............... 604/902, 93.01, 264, 523, 528, 529
See application file for complete search history.

(56) References Cited

U.S. PATENT DOCUMENTS

| | | | |
|---|---|---|---|
| 4,391,276 A | 7/1983 | Lazarus | |
| 4,747,840 A | 5/1988 | Ladika et al. | |
| 4,767,404 A * | 8/1988 | Renton | 604/48 |
| 4,795,439 A * | 1/1989 | Guest | 604/43 |
| 5,061,257 A | 10/1991 | Martinez | |
| 5,423,882 A | 6/1995 | Jackman et al. | |
| 5,433,708 A | 7/1995 | Nichols et al. | |
| 5,437,288 A * | 8/1995 | Schwartz et al. | 600/585 |
| 5,522,873 A | 6/1996 | Jackman et al. | |
| 5,542,928 A | 8/1996 | Evans et al. | |
| 5,611,777 A | 3/1997 | Bowden et al. | |
| 5,718,692 A | 2/1998 | Schon et al. | |
| 5,782,811 A | 7/1998 | Samson et al. | |
| 5,876,398 A | 3/1999 | Mulier et al. | |
| 5,913,854 A | 6/1999 | Maguire et al. | |
| 5,916,193 A | 6/1999 | Stevens | |
| 5,935,102 A | 8/1999 | Bowden et al. | |
| 6,197,014 B1 * | 3/2001 | Samson et al. | 604/524 |
| 6,235,044 B1 | 5/2001 | Root et al. | |

(Continued)

FOREIGN PATENT DOCUMENTS

| EP | 0810003 A | 12/1997 |
|---|---|---|
| EP | 1197239 A | 4/2002 |

(Continued)

OTHER PUBLICATIONS

International Search Report for PCT/US07/69177 filed May 17, 2007, and Written Opinion of ISA, dated Apr. 28, 2008.

(Continued)

*Primary Examiner* — Theodore Stigell
(74) *Attorney, Agent, or Firm* — Wiley Rein LLP

(57) ABSTRACT

The invention encompasses a catheter having an outer surface, a distal end, and at least one interior lumen, wherein the outer surface includes multiple aspiration passageways in fluid communication with an interior lumen. A preferred embodiment comprises multiple aspiration passageways formed into a helical pattern.

39 Claims, 3 Drawing Sheets

U.S. PATENT DOCUMENTS

| | | |
|---|---|---|
| 6,533,763 B1 | 3/2003 | Schneiter |
| 6,635,027 B1 * | 10/2003 | Cragg et al. .................... 604/22 |
| 6,755,813 B2 * | 6/2004 | Ouriel et al. .................. 604/537 |
| 2003/0023230 A1 | 1/2003 | Lewis et al. |
| 2004/0054351 A1 | 3/2004 | Deniega et al. |

FOREIGN PATENT DOCUMENTS

| | | | |
|---|---|---|---|
| EP | 1852138 A | | 11/2007 |
| JP | 2002/017868 | | 1/2002 |
| JP | 2005/000553 | | 1/2005 |
| WO | WO 01/13984 | * | 3/2001 |
| WO | WO-01/13984 | | 3/2001 |
| WO | 2005/120623 A | | 12/2005 |

OTHER PUBLICATIONS

Extended European Search Report for EP07783893, corresponding to PCT/US2007/069177, dated Jun. 10, 2009.

\* cited by examiner

CATHETER WITH ASPIRATION PASSAGEWAY

CROSS-REFERENCE TO RELATED APPLICATIONS

This application claims the benefit of U.S. provisional application No. 60/800,861, filed 17 May 2006, which is hereby incorporated by reference as though fully set forth herein.

BACKGROUND OF THE INVENTION a. Field of the Invention

The instant invention relates to catheters having an outer surface with multiple aspiration passageways, through which fluids, such as blood, may flow into an interior lumen of the catheter, such as a drainage lumen, an aspiration lumen, or even the central lumen of the catheter. The pattern, design, placement and number of aspiration passageways, or holes, allows for improved catheter performance during procedures, such as transseptal procedures, where the distal tip commonly becomes occluded, while still maintaining the structural integrity and functionality of the catheter.

b. Background Art

Catheters are used in a variety of medical procedures to gain access to interior regions of the body and to perform a variety of procedures, such as the ablation of targeted tissue areas. During such procedures, a physician must carefully and precisely control the position of the catheter. To achieve more precise control of instruments such as ablation catheters, various guiding introducer catheters have been developed.

Typically, in procedures where introducer catheters are used to guide an ablation catheter to a particular location in the heart, a small incision is first made at an appropriate location, for example, the groin, the arm, or any other location known to those skilled in the art, and then an artery or vein is punctured at a relatively shallow angle with an appropriate needle, for example, a stylet or some other puncturing device known to those skilled in the art. The needle is then partially withdrawn from the artery or vein, and reinserted at a steeper angle A guidewire is inserted into the artery or vein and advanced to a desired region, for example to the heart region. An introducer catheter is directed over the guidewire to the desired portion of the heart. An instrument, often embodied in a separate catheter, to be used for the treatment of the heart or the heart region, for example, an ablation catheter, may then be advanced through the lumen of the first catheter and placed at the desired location to perform the desired procedure.

The specific type of introducer catheter used will depend upon what portions of the heart the operation is being performed on, and accordingly whether a transseptal or retrograde procedure is used. In transseptal procedures, for example, a catheter apparatus is introduced into the right femoral vein and advanced through the inferior vena cava into the right atrium. A puncture is then made through the fossa ovalis in the inter-atrial septum and the apparatus is advanced into the left atrium.

One skilled in the art recognizes the many problems inherent in the use of introducer catheters in such procedures. For example, given the intricate anatomy of the heart, it is possible for the distal end of the introducer catheter to become occluded, particularly if the distal tip becomes pressed against tissue, or in extreme cases, blocked with debris, such as plaque or cholesterol. This problem is particularly pervasive when puncturing the fossa ovalis in the aforementioned transseptal procedure. Furthermore, puncturing the fossa ovalis often causes localized bleeding, which can lead to the coagulation of blood and subsequent clogging of any openings at or near the distal end of the introducer catheter.

Because an ablation catheter, when advancing through an interior lumen of the transseptal introducer catheter, is cooled in part by the flow of blood through introducer's interior lumen, an occluded distal end would impede the flow of blood and interfere with the temperature control of the ablation device. Accordingly, it is desirable to place aspiration passageways in the side of the catheters to ensure that blood or other fluids continuously flow through an interior lumen. These aspiration passageways function as relief holes in the side of the introducer catheter which allow for the flow of blood into an interior lumen and through the catheter when the distal end of the catheter is occluded. Therefore, it is one object of the present invention to provide improved catheters for a variety of transseptal and retrograde procedures, where the design of aspiration passageways prevents the occlusion of the catheter.

BRIEF SUMMARY OF THE INVENTION

It is desirable, when using catheters, to limit the risk of an occlusion impeding the aspiration of blood or other fluids through an interior lumen of the catheter. The present invention therefore relates to a catheter with multiple passageways, or holes, for the aspiration of blood or other fluids produced at puncture sites during, for example, transseptal procedures. The catheter generally comprises an outer surface, an interior lumen, and distal end capable of being inserted into the body, with aspiration passageways traversing the circumferential outer surface of the catheter. The aspiration passageways permit blood or other fluids to flow through the outer surface of the catheter and into an interior lumen. The aspiration passageways may be strategically positioned on the catheter to ensure that even when the distal end of the catheter becomes clogged or occluded, blood or other fluids may still flow into and through a lumen of the catheter. In a preferred embodiment, the aspiration passageways are arranged in a helical pattern, thus reducing the likelihood that all passageways become occluded by certain pieces of debris or loose tissue, or by coagulated blood.

The present invention additionally relates to a method of placing aspiration passageways along the length of a catheter in a helical pattern, where the presence of multiple passageways minimizes the risk of occlusions preventing flow into an interior while still maintaining the structural integrity of the catheter, especially near the distal end where the passageways have been located. The present invention also relates to a method for selecting a composition of materials, typically a polymer composition, for forming the outer surface of a catheter with aspiration passageways. The present invention further relates to methods of using the catheters of the invention, where blood is aspired through at least one aspiration passageway due to the distal end being occluded. In a preferred example, the method encompasses transseptal procedures, but the claimed method can be used in other procedures where tissue is punctured or ablated.

The foregoing and other aspects, features, details, utilities, and advantages of the present invention will be apparent from reading the following description and claims, and from reviewing the accompanying drawings.

DETAILED DESCRIPTION OF THE INVENTION

The headings (such as "Brief Summary") used are intended only for general organization of topics within the disclosure of the invention and are not intended to limit the disclosure of the invention or any aspect of it. In particular, subject matter disclosed in the "Background Art" includes aspects of technology within the scope of the invention and thus may not constitute solely background art. Subject matter disclosed in the "Brief Summary" is not an exhaustive or complete disclosure of the entire scope of the invention or any particular embodiment.

As used herein, the words "preferred," "preferentially," and "preferably" refer to embodiments of the invention that afford certain benefits, under certain circumstances. However, other embodiments may also be preferred, under the same or other circumstances. Furthermore, the recitation of one or more preferred embodiments does not imply that other embodiments are not useful and is not intended to exclude other embodiments from the scope of the invention and no disclaimer of other embodiments should be inferred from the discussion of a preferred embodiment or a figure showing a preferred embodiment.

Figure 1:
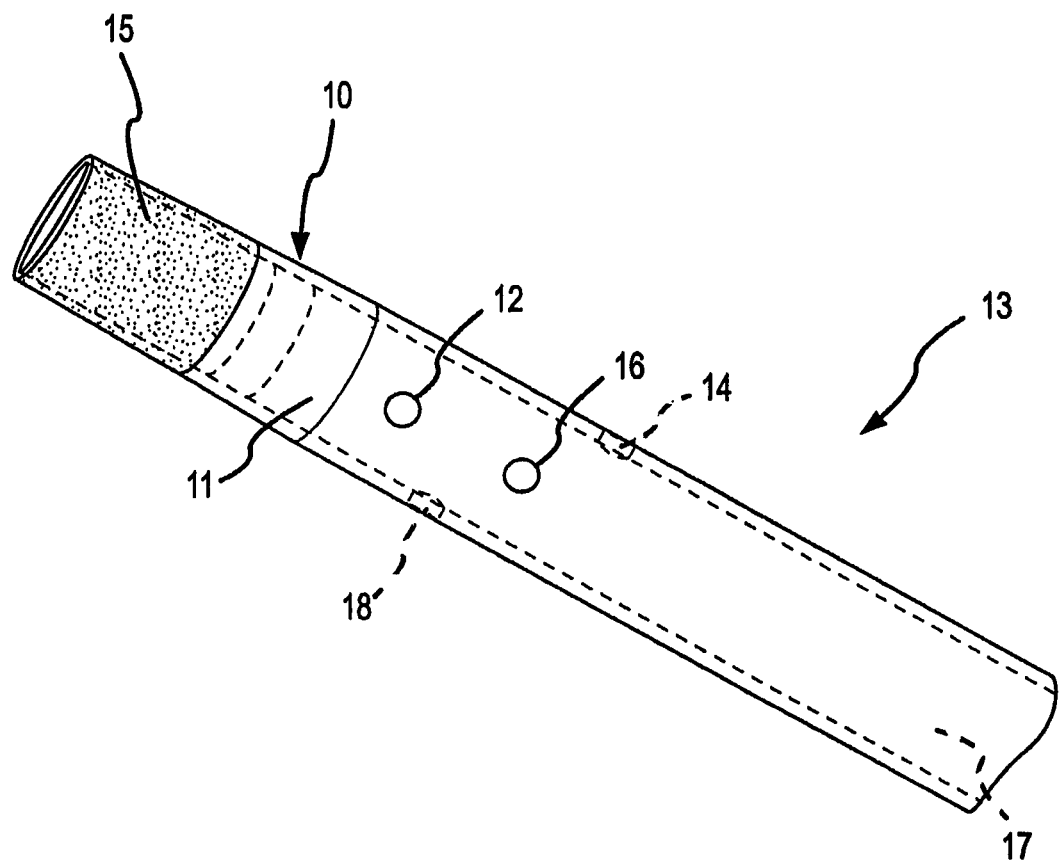
FIG. 1 depicts an isometric view of a catheter according to the claimed invention.
Figure 2:
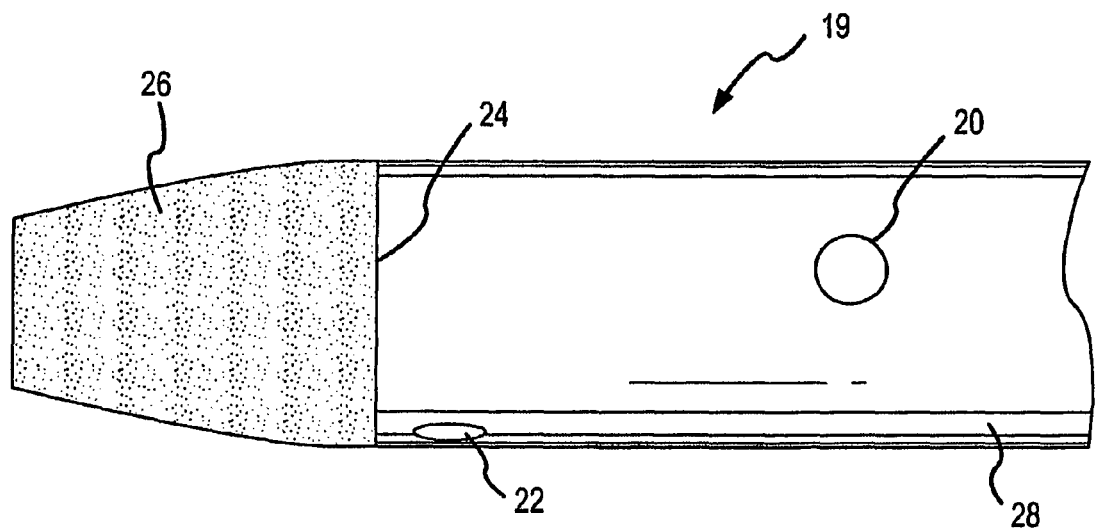
FIG. 2 depicts a catheter with four aspiration passageways drilled in the outer surface, where the four passageways collectively form a helical pattern.
Figure 3:
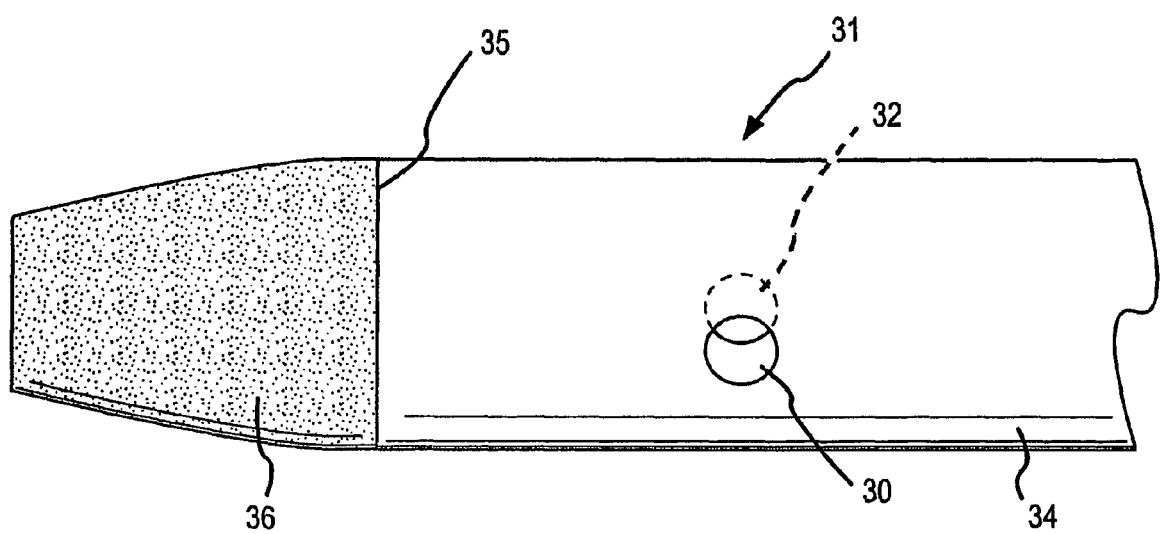
FIG. 3 depicts a catheter with two aspiration passageways drilled in the outer surface and arranged to form a circular pattern.
Figure 4:
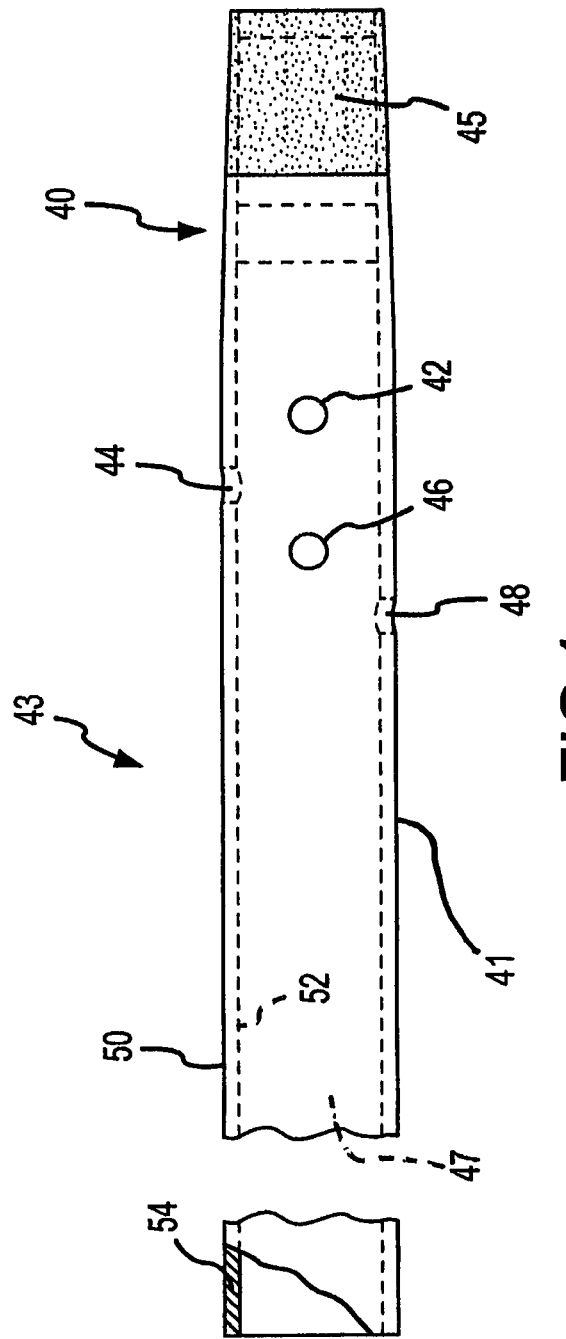
FIG. 4 depicts a catheter having four aspiration passageways drilled in the outer surface of a catheter that lead to an interior lumen, and where the four passageways collectively form a helical pattern.

Briefly referring to the drawings, where FIG. 1 depicts an isometric view of a catheter 13 according to the invention. This catheter includes four aspiration passageways 12, 14, 16, and 18 drilled in the outer surface 11 of the catheter and leading to interior lumen 17. The four passageways collectively form a helical pattern. Attached to the distal end 10 is distal tip 15. FIG. 2 depicts a catheter 19 with four aspiration passageways drilled in the outer surface 28. The four aspiration passageways are in fluid communication with an interior lumen of the catheter. Two aspiration passageways 20, 22 are visible. Two other passageways are not visible in this view. The four passageways collectively form a helical pattern. Attached to the distal end 24 of the catheter 19 is a distal tip 26. FIG. 3 depicts a catheter 31 with two aspiration passages 30, 32 drilled in the outer surface 34 and arranged to form a circular pattern. Attached to the distal end 35 is a distal tip 36. FIG. 4 depicts a catheter 43 having four aspiration passageways 42, 44, 46, and 48 drilled in the outer surface 41 of the catheter, leading to interior lumen 47. The four passageways collectively form a helical pattern. Attached to the distal end 40 is distal tip 45. The outer surface 41 comprises an outer layer 50 and inner layer 52, with a braided member 54 disposed between the two layers.

More specifically, FIG. 1 depicts an isometric view of a transseptal guiding introducer catheter 13 according to the invention, with distal tip 15 at distal end 10. The four aspiration passageways 12, 14, 16, and 18 have been drilled in the outer surface 11 of the catheter and lead to an interior lumen 17. The passageways are in fluid communication with an interior lumen and are located near the distal end or tip of the catheter. For example, the first passageway can be located within one or two or three diameter lengths of the catheter from the distal end, or be positioned next to the closed distal tip or atraumatic tip of the catheter. The figures depicts several examples of the location of the passageways in relation to the distal end of a catheter, but many other locations are envisioned. In FIG. 1, the passageways are spaced or positioned into a helical pattern. Even when, for example, aspiration passageways 14 and 16 are enmeshed in tissue, for example when puncturing the fossa ovalis in transseptal procedures, and thus occluded, due to the helical spacing, passageways 12 and 18 are free of occlusions, therefore allowing blood to flow into the interior lumen 17.

Referring now to FIG. 2, the aspiration passageways are described in greater detail. The outer surface 28 of catheter 19 includes aspiration passageway 20, with a diameter of 0.025 inches. Rotating ninety-degrees along the outer surface of the catheter, and then radially moving 0.5 inches along the outer surface of the catheter and toward the distal end 24 of the catheter, an aspiration passageway 22 of the same diameter is found. Affixed to the distal end is an atraumatic radiopague tip 26. The tip is soft, thus reducing the risk of the catheter poking and damaging tissues, organs, or blood vessels when inside the body. The tip is further visible under fluorescent light, enabling a user to employ fluoroscopy techniques to monitor the location of the catheter in the body.

Referring now to FIG. 3, the outer surface 34 of catheter 31 includes aspiration passageway 30, and rotating one-hundred-eighty degrees, aspiration passageway 32. These two aspiration passageways each have a diameter of about 0.010 to about 0.030 inches (and any size or sub-range of sizes within that range can be selected for use), and the placement of these two passageways accordingly forms a circular pattern. Attached to the distal end 35 is atraumatic radiopague distal tip 36.

Referring now to FIG. 4, a catheter 43 with four aspiration passageways arranged in a helical pattern and radiopague tip 45 is depicted. Beginning at the distal end 40 of the catheter, and moving 0.4 inches away, an aspiration passageway 42 of diameter 0.025 inches is drilled in the outer surface 41 of the catheter. The passageways may be automatically drilled with a laser, manually drilled with a titanium coated drill bit, or with other means known to those skilled in the art. Moving about 0.025 to about 0.10 inches further away from the distal end of the catheter, and then rotating ninety degrees along the outer surface 41 of the catheter, a second aspiration passageway 44 of diameter about 0.01 to about 0.030 inches is drilled in the outer surface 41 of the catheter. Moving another 0.025 to about 0.10 inches, and again rotating ninety degrees along the outer surface 41 of the catheter, aspiration passageway 46, again of diameter 0.025 inches (or from about 0.01 to about 0.030 inches) is drilled in the outer surface 41 of the catheter. The same process of moving 0.05 inches, rotating ninety degrees, and drilling an aspiration passageway of diameter 0.025 inches is repeated to create aspiration passageway 48. Viewed collectively, these four aspiration passageways form a helical pattern, wrapping around the catheter. The aspiration passageways are in fluid communication with the internal lumen 47. Thus, even when the distal tip 45 becomes occluded, blood may flow through one or more of the passageways and into the internal lumen.

FIG. 4 further discloses a catheter with an outer surface comprised of an outer layer 50, inner layer 52, and braided member 54 disposed between the two layers. In this embodiment, the catheter is assembled by placing a braided member over an inner layer, and then covering the inner layer and braids with an outer layer. The presence of braids allows for better transmission of twisting forces along the length of the catheter. Specifically, the braids help prevent the catheter body from kinking when a twisting force is applied to the proximal end of the catheter. The presence of braids, or multiple tubes, does not affect the placement of aspiration passageways. Embodiments of the invention can include those wherein an outer surface comprises multiple sections, including a proximal section being a generally elongated, hollow, straight member, and a distal section being a pre-curved member.

The polymer or polymer compositions used in the outer surfaces of catheters described in FIGS. 1-4 can be selected from any know to those of skill in that art or known to be used or available for use in medical devices and catheters in particular. One of skill in the art is familiar with selecting the appropriate polymer or polymer combinations to achieve the flexibility and lubricity properties desired. In some examples, flexible elastomers, such as polyether block amide—PEBA, such as Pebax®, a registered trademark of Atofina Chemicals, are a preferred polymer for use in the invention and methods especially for the external coating of the catheters. The hardness selected for the outer surface can vary, as in a varying hardness according to the Durometer A or D or Shore A or D scale, known in the art. A preferred Pebax polymer has a hardness of 70 D.

Although various embodiments of this invention have been described above with a certain degree of particularity, those skilled in the art could make numerous alterations to the disclosed embodiments without departing from the spirit or scope of this invention. Accordingly, one skilled in the art will recognize that the claimed invention is not limited to catheters with passageways in helical or circular arrangements, catheters with passageways having about 0.010 to about 0.030 inch diameters, or catheters with two or four holes. For example, aspiration passageways having diameters of 0.040, 0.030, 0.025, 0.020, 0.018, or 0.015 inches are quite suitable for aspirating blood when the distal tip has become occluded. Catheters with six or eight passageways, or passageways arranged in other shapes, both symmetric and non-symmetric, are similarly suitable.

A simple laboratory test, using bovine heart tissue and heparinized porcine blood, may be performed to find other suitable designs according to the claimed invention or to compare the performance of the different claimed embodiments. Prior to testing, positive aspiration should first be established by inundating the distal end of the catheter until the aspiration passageways are no longer visible and then checking for uninhibited aspiration of blood using a luer-lock syringe. Once established, the tip of the distal end is pushed against the heart tissue to completely occlude the tip. In embodiments of the claimed invention, this simple test reveals that positive aspiration of blood is sustained through the aspiration passages, despite the occlusion of the distal tip. This simple test may also reveal that additional or fewer, or larger or smaller, passageways do not always significantly increase or decrease the amount of positive aspiration of blood through the central lumen. Thus, in certain embodiments, such as those depicted in FIGS. 1, 2, and 4, four passageways of a diameter of 0.025 inches may provide the maximum volume of blood that at any one moment can flow through an interior lumen.

Other functional consideration may also play a relevant role in determining aspiration passageway quantities, diameters, or arrangements. For example, given that introducer catheters according to the claimed invention are often used in conjunction with a guidewire, the use of smaller diameter aspiration passageways may be highly desirable, so to minimize the risk of the guidewire becoming lodged in or entangled with the aspiration passages. Accordingly, one skilled in the art, when practicing the invention, may recognize the benefits of choosing an aspiration passageway with a diameter smaller than the guidewire. Because the guidewire typically used in conjunction with transseptal introducers has a diameter of 0.032 inches, a diameter of 0.025 inches, as depicted in FIG. 4 is often preferred.

Though the above embodiments generally relate to transseptal introducer catheters, the claimed invention relates to a variety of other catheter embodiments. For example, the above teachings are equally applicable to retrograde introducer catheters, as one skilled in the art recognizes that the distal tip of such a catheter may become occluded, and that an aspiration passageway, or plurality of aspiration passageways, would allow for the flow of fluids when the distal end is occluded.

Additionally, all directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A kit for use in a transseptal procedure, comprising:
   an introducer catheter comprising a tubular body having a proximal section, a distal section, an outer surface, and at least one interior lumen extending from the proximal section to an opening disposed through a distal end of the distal section configured to received an ablation catheter therethrough, wherein the size of the opening is defined by an inner diameter of the tubular body at the distal end, wherein the outer surface includes multiple aspiration passageways disposed through the outer surface along the distal section, and wherein the aspiration passageways are in fluid communication with the at least one interior lumen and are configured to facilitate continuous fluid flow within the distal section of the tubular body, and
   a guidewire, having a guide wire diameter, over which the introducer catheter may be introduced into a patient's vasculature,
   wherein each of the aspiration passageways has a diameter greater than about 0.01 inches and less than the guide wire diameter.

2. The kit of claim 1, wherein said aspiration passageways are placed in a symmetrical pattern.

3. The kit of claim 1, wherein the outer surface includes an inner layer, an outer layer, and a braided assembly disposed between the inner and outer layers.

4. The kit of claim 3, wherein the introducer catheter is of sufficient length for introduction into a patient and for manipulation from the point of insertion through to a desired location in the heart.

5. The kit of claim 1, wherein the distal end comprises an atraumatic tip.

6. The kit of claim 5, wherein said atraumatic tip is radiopaque.

7. The kit of claim 1, wherein the aspiration passageways are arranged such that they form a helical pattern.

8. The kit of claim 1, wherein the aspiration passageways are arranged such that they form a circular pattern.

9. The kit of claim 1, wherein said aspiration passageways are of a diameter between 0.01 and 0.03 inches.

10. The kit of claim 1, wherein said aspiration passageways are of a diameter of about 0.025 inches.

11. A kit for use in a transseptal procedure, comprising:
an introducer catheter comprising a tubular body having a circumferential outer surface, a proximal section, a distal section, and at least one interior lumen extending from the proximal section to an opening disposed through at distal end of the distal section configured to received an ablation catheter therethrough, wherein the size of the opening is defined by an inner diameter of the tubular body at the distal end, wherein the introducer catheter includes a plurality of aspiration passageways disposed through the outer surface along the distal section, and wherein the aspiration passageways are in fluid communication with the at least one interior lumen, are formed in a helical pattern, and are configured to facilitate continuous fluid flow within the distal section of the tubular body, and
a guidewire, having a guidewire diameter, over which the introducer catheter may be introduced into a patient's vasculature,
wherein said aspiration passageways are of a diameter between 0.010 inches and the guidewire diameter.

12. The kit of claim 11, wherein the outer surface comprises an inner layer, an outer layer, and a braided assembly disposed between the inner and outer layers.

13. The kit of claim 12, wherein the introducer catheter is of sufficient length for introduction into a patient and manipulation from the point of insertion through to a desired location in the heart.

14. The kit of claim 11, wherein to the distal end comprises an atraumatic tip.

15. The kit of claim 14, wherein said atraumatic tip is radiopaque.

16. The kit of claim 14, wherein said atraumatic tip contains one or more of the following chemicals: MDX, hexane, cyclohexanane, and PVC.

17. The kit of claim 11, wherein said outer surface contains a poly ether block amide polymer, alone or in combination with other materials.

18. The kit of claim 11, wherein said introducer catheter contains four aspiration passageways.

19. The kit of claim 11, wherein said introducer catheter contains six aspiration passageways.

20. The kit of claim 11, wherein said introducer catheter contains eight aspiration passageways.

21. The kit of claim 11, wherein said aspiration passageways are of a diameter between 0.01 and 0.03 inches.

22. The kit of claim 11, wherein said aspiration passageways are of a diameter of about 0.025 inches.

23. A kit for use in a transseptal procedure, comprising:
an introducer catheter comprising a tubular body having an outer surface, a proximal section, a distal section, and at least one interior lumen extending from the proximal section to an opening disposed through a distal end of the distal section configured to receive an ablation catheter therethrough, wherein the introducer catheter includes a plurality of aspiration passageways disposed along the distal section and formed in a helical pattern, wherein the aspiration passageways are configured to facilitate continuous fluid flow within the distal section of the tubular body, and
a guidewire, having a guidewire diameter, over which the introducer catheter may be introduced into a patient's vasculature,
wherein the aspiration passageways have a diameter of between 0.01 inches and the guidewire diameter.

24. The kit of claim 23, wherein said aspiration passageways are circumferentially spaced ninety degrees apart.

25. The kit of claim 23, wherein the aspiration passageway closest to the distal end is located on the magnitude of 0.40 inches from said distal end.

26. The kit of claim 23, wherein said aspiration passageways are linearly spaced on the magnitude of 0.05 inches apart.

27. The kit of claim 23, wherein said introducer catheter is a transseptal introducer.

28. The kit of claim 23, wherein said introducer catheter contains four aspiration passageways.

29. The kit of claim 23, wherein said introducer catheter contains six aspiration passageways.

30. The kit of claim 23, wherein said introducer catheter contains eight aspiration passageways.

31. The kit of claim 23, wherein said outer surface contains an inner layer, an outer layer, and a braided assembly between the inner and outer layers.

32. The kit of claim 23, wherein said outer surface comprises multiple sections, the proximal section comprising a generally elongated, hollow, straight member, and the distal section comprising a pre-curved member.

33. The kit of claim 32, wherein said proximal section is of sufficient length for introduction into the patient and for manipulation from the point of insertion through to a desired location within the heart.

34. The kit of claim 23, wherein the distal end comprises an atraumatic tip.

35. The kit of claim 34, where said atraumatic tip is radiopaque.

36. The kit of claim 34, wherein said atraumatic tip contains one or more of the following chemicals: MDX, hexane, cyclohexanane, and PVC.

37. The kit of claim 23, wherein said outer surface contains a poly ether block amide polymer, alone or in combination with other materials.

38. The kit of claim 23, wherein said aspiration passageways are of a diameter between 0.01 and 0.03 inches.

39. The kit of claim 23, wherein said aspiration passageways are of a diameter of about 0.025 inches.

\* \* \* \* \*